United States Patent [19]

Hoffman

[11] 4,268,459

[45] May 19, 1981

[54] CYCLIC DIPHOSPHONATES

[75] Inventor: Joseph A. Hoffman, Bridgewater, N.J.

[73] Assignee: American Cyanamid Company, Stamford, Conn.

[21] Appl. No.: 79,689

[22] Filed: Sep. 28, 1979

Related U.S. Application Data

[63] Continuation-in-part of Ser. No. 700,996, Jun. 29, 1976, abandoned.

[51] Int. Cl.³ .......................... C07F 9/15; C08K 5/53
[52] U.S. Cl. ......................... 260/927 R; 260/45.7 P
[58] Field of Search .................................... 260/927 R

[56] References Cited

U.S. PATENT DOCUMENTS

| | | | |
|---|---|---|---|
| 3,511,857 | 5/1970 | Baranaueckas et al. | 260/927 R |
| 3,515,776 | 6/1970 | Baranaueckas et al. | 260/927 R |
| 3,890,409 | 6/1975 | Mayerhoefer et al. | 260/927 R |
| 3,922,323 | 11/1975 | Reese et al. | 260/927 R |

*Primary Examiner*—Anton H. Sutto
*Attorney, Agent, or Firm*—Bruce F. Jacobs

[57] ABSTRACT

Phosphonate compounds of the formula

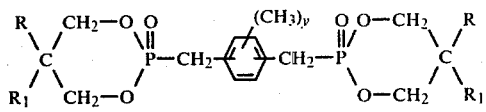

wherein R is hydrogen or methyl, $R_1$ is hydrogen, methyl or ethyl, and y is an integer from 0 to 2, are useful as flame retardants for thermoplastic polymers, especially linear thermoplastic polyesters.

7 Claims, No Drawings

CYCLIC DIPHOSPHONATES

CROSS REFERENCE TO RELATED APPLICATIONS

This application is a continuation-in-part of U.S. Ser. No. 700,996, filed June 29, 1976 now abandoned.

BACKGROUND OF THE INVENTION

This invention relates to novel cyclic phosphonate esters which are useful for flame-proofing thermoplastic polymers, particularly polyolefins and polyesters.

The use of cyclic esters of diphosphonic acids for flame-proofing thermoplastic polymers such as polyurethanes, polyesters, polyacrylates, polymethacrylates, polyamides and polyvinyl chloride is disclosed by Baranauckas et al. in U.S. Pat. Nos. 3,511,857 and 3,515,776. Baranauckas et al. also disclose the use of acrylic esters of diphosphonic acids in U.S. Pat. Nos. 3,538,196 and 3,737,397 for similar purposes. However, the diphosphonate esters of Baranauckas et al. must contain from 2 to about 32 hydroxyl groups for further reaction with other polyfunctual intermediates in the polymer substrate, such as polybasic acids and anhydrides, alkyd resins, toluene diisocyanate, and the like.

The use of the cyclic ethylene and trimethylene esters of benzylphosphonic acid as flameproofing agents is disclosed in German Pat. No. 2,153,149.

U.S. Pat. No. 3,922,323 of Reese et al. discloses various halogen-containing cyclic phosphonate esters and their use as flame retardants for unsaturated polyesters. However, when these compounds are used as flame retardants for linear thermoplastic polyesters, they must be processed at much higher temperatures which results in the degradation of the polyester as evidenced by a drastic reduction in the melt viscosity of the polymer.

U.S. Pat. No. 3,890,409 of Mayerhoefer et al. discloses various cyclic diphosphates and diphosphites as flame retardants.

However, none of these materials has proven to be completely satisfactory and the search still continues for a satisfactory flame retardant compound for the flame-proofing of thermoplastic polymers, particularly polyolefins and polyesters.

SUMMARY OF THE INVENTION

It has been discovered that compounds having the formula $$\begin{array}{c}R\\ \diagdown\\ \diagup\\ R_1\end{array}\!\!C\!\!\begin{array}{c}CH_2-O\\ \diagdown\\ \diagup\\ CH_2-O\end{array}\!\!\overset{O}{\underset{\parallel}{P}}\!-\!CH_2\!-\!\!\!\bigotimes_{(CH_3)_y}\!\!\!-\!CH_2\!-\!\overset{O}{\underset{\parallel}{P}}\!\!\begin{array}{c}O-CH_2\\ \diagup\\ \diagdown\\ O-CH_2\end{array}\!\!C\!\!\begin{array}{c}R\\ \diagup\\ \diagdown\\ R_1\end{array}$$

wherein R is hydrogen or methyl, $R_1$ is hydrogen, methyl or ethyl, and y is an integer of from 0 to 2, inclusive, are effective flame retardants for thermoplastic polymers, especially linear thermoplastic polyesters.

Preferred compounds of this invention are those wherein y is 0 and R is methyl, and $R_1$ is as defined, and the phosphonate groups are para to each other.

DESCRIPTION OF THE PREFERRED EMBODIMENTS

The cyclic phosphonate esters of the present invention may be prepared by several well-known methods. In one method an alkali metal salt of a cyclic ester of phosphonic acid is reacted with an equivalent amount of a suitable halomethyl-substituted benzene compound as illustrated in the general reaction shown below wherein Y is a halo atom, such as bromo or chloro.

$$YCH_2\!-\!\!\!\bigotimes_{(CH_3)_y}\!\!\!-\!CH_2Y + 2\,Na\!-\!\overset{O}{\underset{\parallel}{P}}\!\!\begin{array}{c}O-CH_2\\ \diagdown\\ \diagup\\ O-CH_2\end{array}\!\!C\!\!\begin{array}{c}R\\ \diagup\\ \diagdown\\ R_1\end{array}\longrightarrow$$

$$\begin{array}{c}CH_3\\ \diagdown\\ \diagup\\ R_1\end{array}\!\!C\!\!\begin{array}{c}CH_2O\\ \diagdown\\ \diagup\\ CH_2O\end{array}\!\!\overset{O}{\underset{\parallel}{P}}\!-\!CH_2\!-\!\!\!\bigotimes_{(CH_3)_y}\!\!\!-\!CH_2\!-\!\overset{O}{\underset{\parallel}{P}}\!\!\begin{array}{c}OCH_2\\ \diagup\\ \diagdown\\ OCH_2\end{array}\!\!C\!\!\begin{array}{c}R\\ \diagup\\ \diagdown\\ R_1\end{array} + 2NaY$$

The intermediate alkali metal salt of the cyclic ester of phosphonic acid may be prepared by reacting the cyclic ester with an equimolar amount of an alkali metal hydride, such as sodium, potassium, or lithium hydride, in an inert dry solvent, such as dry benzene, at temperatures between 20° C. and 60° C. until the reaction is completed.

Illustrative examples of alkali metal salts of cyclic esters of phosphonic acid which may be used to prepare the compounds of this invention include the sodium, potassium and lithium salts of cyclic trimethylene phosphonate, 2,2-dimethyltrimethylene phosphonate and 2-methyl-2-ethyl-trimethylene phosphonate.

The intermediate cyclic esters of phosphonic acid may be prepared by reacting equimolar amounts of phosphorus trichloride, a suitable diol, and a lower alcohol, such as ethanol, as described by McConnell et al., J. Org. Chem. Vol. 24, pages 630–635 (1959) which is hereby incorporated herein by reference. (In the prior art literature the intermediate cyclic phosphonates are also called cyclic hydrogen phosphites.)

The intermediate cyclic esters of phosphonic acid may also be prepared by hydrolyzing the corresponding cyclic alkylene chlorophosphites as described by Zwierzal, Can. J. Chem. 45, 2501 (1967). Lucas et al., J. Am. Chem. Soc. 72, 5491 (1950) describe the preparation of cyclic esters of phosphonic acid by reacting a diol with phosphorus trichloride and the hydrolysis of the resultant chlorophosphites to the cyclic phosphonic acid ester under carefully controlled conditions.

Illustrative of intermediate cyclic esters of phosphonic acid which may be employed to produce my novel cyclic phosphonate esters are the following:

cyclic 2,2-dimethyltrimethylene phosphonate $$\begin{array}{c}CH_3\\ \diagdown\\ \diagup\\ CH_3\end{array}\!\!C\!\!\begin{array}{c}CH_2-O\\ \diagdown\\ \diagup\\ CH_2-O\end{array}\!\!\overset{O}{\underset{\parallel}{P}}\!-\!H$$

and cyclic 2-methyl-2-ethyltrimethylene phosphonate $$\begin{array}{c}CH_3\\ \diagdown\\ \diagup\\ CH_3CH_2\end{array}\!\!C\!\!\begin{array}{c}CH_2-O\\ \diagdown\\ \diagup\\ CH_2-O\end{array}\!\!\overset{O}{\underset{\parallel}{P}}\!-\!H$$

The intermediate halomethylated benzene compounds may conveniently be prepared by reacting the corresponding benzene with formaldehyde and a hydrogen halide e.g. hydrogen chloride, hydrogen bromide etc., according to known procedures such as those disclosed in U.S. Pat. Nos. 2,945,894: 2,951,100;

2,973,391; and 3,069,480. Alternatively, chlorination of the alkyl group or groups of the appropriate methyl benzene in the presence of suitable catalysts, see U.S. Pat. No. 2,926,202, or with chlorine absorbed on zeolite and under reactive conditions, see U.S. Pat. No. 2,956,084, may be effected.

In another method for prparing the cyclic phosphonate esters of this invention, an alkyl cyclic alkylene phosphite ester can be reacted with an equivalent amount of a suitable halomethyl-substituted benzene compound by the well-known Arbuzov reaction.

The preparation of various alkyl cyclic alkylene phosphite esters which may be used for this method of preparation as disclosed by Arbuzov et al. is reported in C. A. 47, 9900 et seq.

In another method of preparing the cyclic phosphonate esters of this invention, an intermediate ester may be prepared by reacting a trialkyl phosphite with a suitable halomethyl-substituted benzene compound by the above-mentioned Arbuzov reaction and than transesterifying the product (II) with a suitable diol. This method is illustrated below:

merization media during the polymer manufacture, provided the ingredients, catalysts, etc., therein are inert thereto.

The thermoplastic polymers into which the novel compounds of this invention may be incorporated to produce the novel compositions of the instant invention are generally those produced from at least one ethylenically unsaturated monomer, wherein the monomer, or monomers, are polymerized, by any known method, via the ethylenic unsaturation therein. Preferred examples of polymers conforming to this definition include the polyolefins i.e. those polymers produced from the α-olefins such as ethylene, propylene, pentene-1, etc., including copolymers of ethylene, propylene, pentene-1, etc., with each other and with such monomers as vinyl acetate, etc., and homopolymers thereof, i.e., polyethylene; polypropylene, polypentene-1, etc., and linear aromatic polyesters such as polyethylene terephthalate; polybutylene terephthalate; poly)1,4-cyclohexanedimethylene)terephthalate; poly(1,4-cyclohexanedimethylene)terephthalate, etc; the polyalkylene oxides such as polyethylene oxide; nylon; butadi-

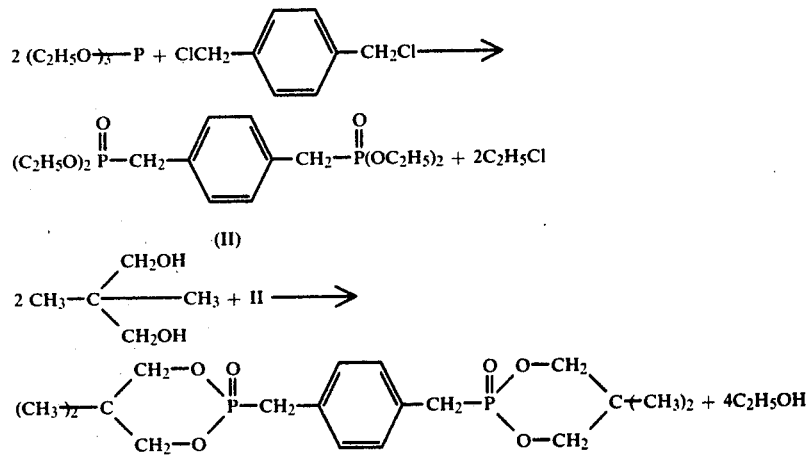

In still another method of preparation of the cyclic phosphonate esters of the instant invention, a suitably substituted benzyl phosphonic dihalide can be reacted with a glycol, as illustrated below for the preparation of compound III.

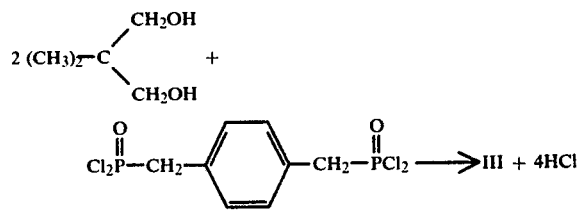

The preparation of benzyl phosphonic dihalides is described by Kosolopoff in "Organophosphorus Compounds", page 66, John Wiley and Sons, Inc., New York (1958).

The cyclic phosphonate esters of this invention may be incorporated into thermoplastic polymers by any known method. For example, the compound may be combined with the polymer by milling the materials on a two-roll mill, mixing in a Banbury mixer, extrusion, injection molding, and the like. The cyclic phosphonate ester may also be incorporated by adding it to the polyene polymers such as the so-called "impact polymers", i.e., acrylonitrile-butadiene-styrene polymers; acrylonitrile-styrenemethyl methacrylate grafted polybutadiene, etc. Further examples of applicable polymers which may be flame-proofed using my novel compounds are set forth in U.S. Pat. No. 3,284,543 which is hereby incorporated herein by reference.

The compounds may be incorporated into the thermoplastic polymers to which they are to impart flame retardance in flame-retarding amounts which generally range from about 5% to about 30% by weight, based on the weight of the polymer.

The instant flame-retardant compounds may be utilized as such or in conjunction with various flame-retardant additives such as the ammonium polyphosphates, see column 3, lines 25-57 of U.S. Pat. No. 3,835,119, hereby incorporated herein by reference, in the ratio of flame-retardant compound to ammonium polyphosphate of 2:1 to 1:3. Additionally, to the ammonium polyphosphate-flame-retardant compound mixture may be added a metal oxide such as titanium dioxide in amounts ranging from about 1 to about 5 percent, by weight, based on the weight of the polymer. These metal oxides perform synergistically with the ammonium polyphosphate and flame-retardant compound to minimize dripping of the polymer to which they are added when it is burning and before it extinguishes itself, as can be readily appreciated from a perusal of the above U.S. Pat. No. 3,835,119.

It is within the scope of the present invention to incorporate such ingredients as plasticizers, dyes, pigments, fillers, stabilizers, antioxidants, antistatic agents etc., into my novel compositions without detracting from the advantageous properties exhibited thereby.

The following examples are set forth for purpose of illustration only and are not to be construed as limitations on the present invention except as set forth in the appended claims. All parts and percentages are by weight unless otherwise specified.

EXAMPLE 1

Phosphorus trichloride (274 parts; 2.0 moles) is added dropwise to a solution of 2,2-dimethyl-1,3-propanediol (208 parts; 2.0 moles) in absolute ethanol (92 parts; 2.0 moles) while cooling to maintain the temperature at 25° C. When the addition is completed, the reaction mixture is stirred at 25° C. for 3 hours while passing a stream of nitrogen gas therethrough. The reaction mixture is then warmed on a steam bath to remove hydrogen chloride and ethyl chloride. The clear solution is concentrated under vacuum and the residual clear oil is distilled under vacuum to obtain 258 parts (86% of theory), b.p. 113°–114° C. at 1 mm. pressure, of a product which is identified by infrared absorption spectroscopy as:

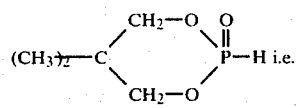

cyclic 2,2-dimethyltrimethylene phosphonate.

A solution of the cyclic 2,2-dimethyltrimethylene phosphonate (33 parts; 0.22 mole) in 150 mls of dry benzene is added dropwise to a slurry of 9.3 parts of a 57%, by weight, dispersion of sodium hydride in oil (5.3 parts real; 0.22 mole) in 150 mls. of dry benzene while keeping the temperature below 30° C. The reaction mixture is then heated at 40°–45° C. for 2 hours and a solution of 1,4-bis(chloromethyl)-benzene (17 parts; 0.097 mole) in 150 mls. of dry benzene is added rapidly while holding the temperature at 35°–40° C. The reaction mixture is stirred at 35°–40° C. for 1 hour after completing the addition and then heated at reflux for 2 days. The reaction mixture is cooled and the insoluble material is separated by filtration and dried to obtain 55 parts of white solid. This material is slurried in 400 mls. of warm water for ½ hour, filtered and dried under vacuum to obtain 38 parts of material. Recrystallization of this material from N,N-dimethylacetamide gives 35 parts of white solid, m.p. 301°–303° C. which is identified by microanalysis as

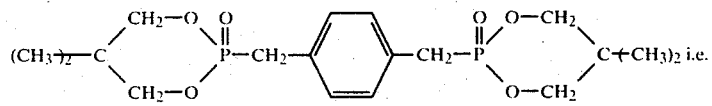

the bis cyclic(2,2-dimethyltrimethylene)ester of 1,4-phenylenedimethylenediphosphonic acid.

EXAMPLE 2

A solution of the sodium salt of cyclic 2,2-dimethyltrimethylene phosphonate (0.2 mole) is prepared by reacting cyclic 2,2-dimethyltrimethylene phosphonate (30.0 parts; 0.2 mole) in 150 mls. of dry dimethylformamide with 8.4 parts of a 57% by weight dispersion of sodium hydride in oil (4.8 parts real; 0.2 mole) while keeping the temperature below 30° C.

A solution of 1,4-bis(chloromethyl)-2,5-dimethylbenzene (20 parts; 0.1 mole) in 150 mls. of dry dimethylformamide is added to said solution of the sodium salt and the temperature is allowed to rise. After the addition is completed and the exotherm subsides, the reaction mixture is heated at 60°–65° C. for 15–18 hours, cooled to room temperature and filtered to separate a precipitate. The filter cake is rinsed with dimethylformamide, partially dried and then fully dried in a vacuum oven. The dried cake is then slurried in warm water, filtered, rinsed with water and dried in a vacuum oven to obtain 32 parts of a white solid which melts at 231°–233° C. after recrystallization from isopropanol and is identified as

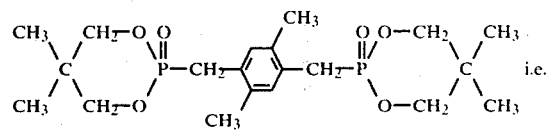

the bis cyclic(2,2-dimethyltrimethylene)ester of [(2,5-dimethyl-1,4-phenylene)dimethylene]diphosphonic acid.

EXAMPLE 3

A mixture of ethyl cyclic trimethylene phosphite (12.0 parts; 0.08 mole), prepared according to the method of Arbusov et al., using ethanol instead of methanol, and 1,4-bis(chloromethyl)benzene (7.0 parts; 0.04 mole) in 25 mls. of dry dimethylformamide is heated at reflux for one hour and then cooled to room temperature and allowed to stand overnight. The solid precipitate is separated by filtration and recrystallized from dimethylformamide to obtain a pale yellow solid, m.p. 303°–305° C., which is identified by infrared absorption spectroscopy as

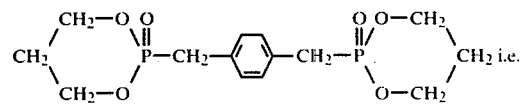

the bis cyclic(trimethylene)ester of p-phenylenedimethylenediphosphonic acid.

EXAMPLE 4

Following the procedure of Example 1, the sodium salt of cyclic 2-methyl-2-ethyl-trimethylene phosphonate is reacted with bis(bromomethyl)benzene to obtain bis cyclic(2-methyl-2-ethyltrimethylene)ester of 1,4-phenylenedimethylenediphosphonic acid.

COMPARISON EXAMPLE A

The sodium salt of cyclic 2,2-dimethyltrimethylene phosphonate is prepared as described in Example 1, but the mixture is only stirred at 40° C. for 15 minutes after the cyclic phosphonate is added. The mixture is diluted with dry benzene to a total volume of 800 mls. and bis(bromomethyl)durene (31.0 parts; 0.097 mole) added rapidly under nitrogen as a solid. Upon completion of the addition of the bis(bromomethyl)durene, the reaction mixture is stirred under nitrogen at 40° C. for 3 hours and then refluxed for 16 hours. The reaction mixture is then cooled to room temperature and filtered to separate the insolubles. The filter cake is washed with benzene, dried under vacuum, slurried several times with water and dried in a vacuum oven to obtain 40 parts of white solid, which melts at 256°–258° C. after recrystallization from isopropanol. The product is identified by elemental analysis as

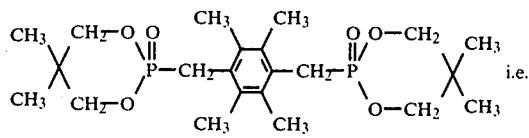

the biz cyclic(2,2-dimethyltrimethylene)ester of [(tetramethyl-p-phenylene)dimethylene]diphosphonic acid.

COMPARISON EXAMPLE B

The compound below of Example 12 of U.S. Pat. No. 3,922,323 was prepared as follows:

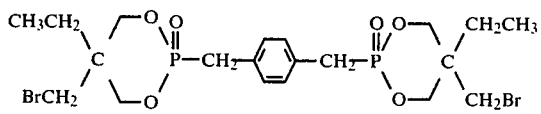

A. Preparation of 3-Ethyl-3-Hydroxymethyl Oxytane (I), following the procedure of Pattison, J. Am. Chem. Soc. 79, 3455 (1957).

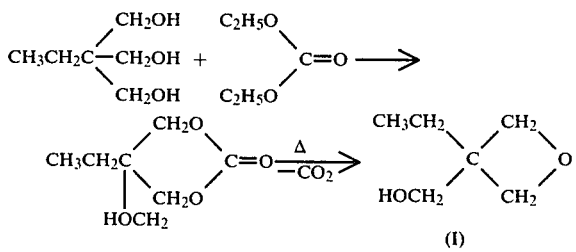

To a 1-liter flask equipped with a 6" Vigreaux column and a distillation head was added 268 grams, 2.0 moles, of trimethylolpropane, 236 grams, 2.0 moles, of diethylcarbonate, and 0.2 gram of potassium hydroxide. The mixture was heated at 100° C. for 30 minutes with stirring and then distilled, keeping the pot temperature between 140° C. and 150° C. and the head temperature between 76° C. and 79° C. until distillation of ethanol ceased. The pressure was then reduced gradually to 50 mm Hg and the distillation continued. When distillation again ceased, the temperature of the mixture was slowly raised to 200°–220° C. whereupon evolution of carbon dioxide was rapid and most of the compound distilled at 90°–93° C. at 40–60 mm Hg. Redistillation at 65° C. and 0.5 mm Hg gave 148 grams, 64% of theory, of 3-ethyl-3-hydroxymethyl oxytane (I); literature b.p. 84° C. at 2.8 mm Hg.

B. Preparation of 2-Ethyl-2-Bromomethyl-1,3-Propanediol (II), according to the procedure of Reiff et al., Liebigs Ann. Chem. 365 (1973).

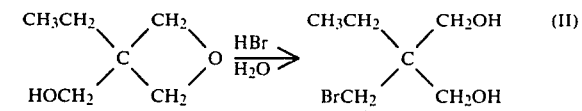

To a 500 ml., 3-necked flask equipped with a stirrer, reflux condenser and addition funnel was added 3-ethyl-3-hydroxymethyl oxytane (I), 148 grams, and then slowly a 48% aqueous solution of hydrogen bromide (185 grams) was added thereto. The reaction mixture was heated for 8 hours at 90° C. and then cooled to room temperature. To this mixture was then added 300 grams of ice water and the resulting white precipitate was filtered and dried in a vacuum oven for 2 days at 60° C. There was obtained 197 grams of 2-ethyl-2-bromomethyl-1,3-propanediol, m.p. 78°–80° C. (literature 81°–82° C.), in 60% yield.

C. Preparation of 2-Ethyl-2-Bromomethyl Trimethylene Ethyl Phosphite (IV)

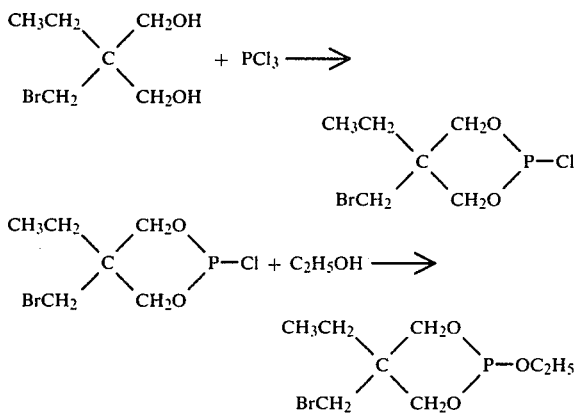

To a 1-liter, 3-necked flask equipped with a stirrer, reflux condenser and an addition funnel was added a solution of 110 grams, 0.56 mole, of 2-ethyl-2-bromomethyl-1,3-propanediol in 200 ml. of methylene chloride. To this solution, under a nitrogen atmosphere, was added 48.8 ml., 0.56 mole, of phosphorus trichloride over a period of 30 minutes. The mixture was then refluxed until evolution of hydrogen chloride ceased. The mixture was then distilled to remove low boiling materials, including unreacted phosphorus trichloride and solvent, at 50 mm Hg and 60° C. to give a residue of 154 grams of intermediate phosphorchloridite (III).

A solution of 27 grams, 0.058 mole, of ethanol and 59 grams, 0.59 mole, of triethylamine in 1200 ml. of anhydrous diethyl ether was cooled in an ice bath and the intermediate (III) added slowly thereto. The mixture was stirred for 1 hour at room temperature and filtered. The ether was evaporated under reduced pressure and the residue distilled to give 97 grams of (IV), b.p. 93° C. at 0.35 mm Hg.

D. Preparation of p-Phenylenedimethylene)bis[2-ethyl-2-(bromomethyl)-trimethylene Phosphonate], (V)

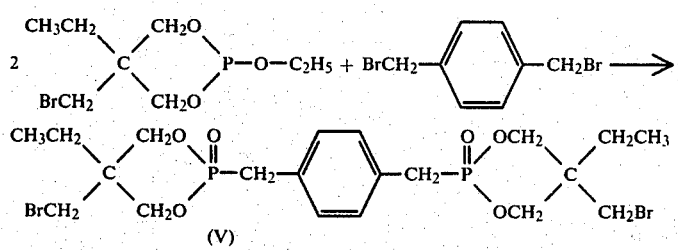

(V)

2-Ethyl-2-bromomethyltrimethylene ethyl phosphite (IV), 97 grams, 0.372 mole and α,α'-dibromo-p-xylene, 48.9 grams, 0.186 mole, were mixed in a 500 ml. flask equipped with an air condenser and a nitrogen inlet tube. The mixture was slowly heated to 100° C., at which time the reaction was completed, leaving a white solid. The solid was washed with two 100 ml. portions of benzene-acetone (50/50) and then ground in a morter to a fine powder. The powder was boiled in benzene-acetone (50/50) for several minutes, cooled to 10° C., filtered and dried in a vacuum oven at 50° C. for 12 hours. There was obtained 109 grams of product, m.p. 242° C.

Evaulation of Flame Retardants

EXAMPLE A

A. Alone in Polypropylene

To polypropylene containing 0.1% of pentaerythrityl tetrakis (3,5-di-t-butyl-4-hydroxyphenyl)propionate and 0.25% of distearylthiodipropionate as antioxidants, flame-retardant material is added by milling the admixture at 175° C. on a standard plastic mill to provide a compounded polypropylene composition containing 15%, by weight, of the flame retardant to be tested; the resultant mixture is compression molded at 200° C. to provide test bars, 5"×0.5"×0.125", which are tested for flammability according to the procedure described in ASTM D-635. The results obtained in terms of the average distance burned (AEB) and average time of burning (ATB) prior to flame extinguishment are given in Table I, below.

A control sample without flame retardant continues to burn, after removal of the ignition source, until all of the sample is consumed.

TABLE I

| Example | Flame Retardant | ASTM D-635 AEB | ATB | Observation |
|---|---|---|---|---|
| 5 | Product of Example 1 | 12.5 mm | 20 secs. | self-extinguishing |
| 6 | Product of Example 2 | 25 mm | 180 secs. | self-extinguishing |
| 7 | Control | — | — | burned completely |
| 8 | Product of Comparison Example B | 40 mm | 330 secs. | self-extinguishing |

EXAMPLE B

B. Combinations with Ammonium Polyphosphate and Titanium Dioxide in Polypropylene The flame retardants are incorporated into polypropylene, as described in A, above, at 12% concentration with 17% ammonium polyphosphate and 1% titanium dioxide. The molded sample, 5"×0.5"×0.125", is tested by the Underwriters' Laboratory Test UL-94 for vertical burning. The flammability is rated according to the following definitions:

V-0: flame extinguishes in 0–5 seconds; non-dripping or if dripping, the drippings do not ignite cotton batting.

V-1: flame extinguishes in 6–25 seconds; non-dripping, or if dripping, the drippings do not ignite cotton batting.

V-2: flame extinguishes in 0–25 seconds; drips and ignites cotton batting.

The results are set forth in Table II, below.

TABLE II

| Example | Flame Retardant | UL-94 Rating |
|---|---|---|
| 9 | Product of Example 1 | V-0 |
| 10 | Product of Example 2 | V-0 |
| 11 | Product of Example 3 | V-0 |
| 12 | Product of Comparison Example A | V-2 |
| 13 | Product of Comparison Example B | V-2 |

EXAMPLE C

Evaluation of Flame Retardants in Poly(ethylene terephthalate)

Twenty-gram samples of poly(ethylene terephthalate) (PET) containing 10% of flame retardant are dried in vacuo at 80° C. for 24 hours and melted in a test tube at 290° C. under nitrogen atmosphere. The molten sample is stirred for 10 minutes at this temperature and cooled under nitrogen. The polymer is removed from the test tube and micromilled on a laboratory Wiley-type mill. The milled sample is dried in vacuo overnight and laminated to a 5"×5" pieces of fiber glass cloth using a Carver laboratory press. Compression molding conditions are: 30 second at 288° C. (550° F.) and 3,000 psi. The laminate is quenched in cold water and dried.

Laminate samples, 2"×5"×0.025", are placed in a General Electric flammability gauge (oxygen index apparatus), and the oxygen index is measured according to ASTM D 2863-70. A similar PET/fiber glass laminate control sample is also tested for comparison. In this test, the higher the oxygen index the better the flame-retardance. The results obtained are as follows:

| Example | Flame-Retardant | Oxygen Index |
|---|---|---|
| 14 | Product of Example 1 | 23.7 ± 0.4 |
| 15 | Product of Example 2 | 24.0 |

-continued

| Example | Flame-Retardant | Oxygen Index |
|---|---|---|
| 16 | Control - none | 19.4 |
| 17 | Product of Comparison Example A | 22.9 |
| 18 | Product of Comparison Example B | 23.0 ± 0.3 |

EXAMPLE D

Effect of Flame Retardants on the Melt Viscosity of Poly(ethylene Terephthalate)

Pre-dried samples of poly(ethylene terephthalate) containing 10% by weight of the compounds of Example 1 and Comparison Example B were melted at 290° C. and kept in the oil bath of a Haake Inc. "Roto visco" viscometer for 10 minutes at 290° C. before measuring the viscosity. The instrumental units give the apparent viscosity of the samples. Results are shown below.

| Example | Flame Retardant | Apparent Viscosity (Instrumental Units) | Decrease in Viscosity, % |
|---|---|---|---|
| 19 | Control - None | 784 ± 35 | — |
| 20 | Product of Example 1 | 647 ± 22 | 17 |
| 21 | Product of Comparative Example B | 319 ± 57 | 59 |

This viscosity data shows that the compound of the prior art caused a large decrease in the melt viscosity of the polymer which means that it seriously degraded the polymer, whereas the compound of the present invention only slightly degraded the poly(ethylene terephthalate).

What is claimed is:

1. A compound having the formula

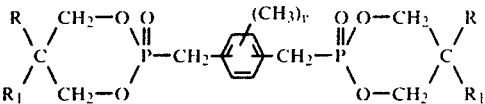

wherein R is hydrogen or methyl; $R_1$ is hydrogen, methyl, or ethyl; and y is an integer from 0 to 2 inclusive.

2. The compound of claim 1 having the phosphonate groups para to each other.

3. The compound of claim 1 wherein R is methyl, y is 0, and the phosphate groups are para to each other.

4. The compound of claim 1 having the formula:

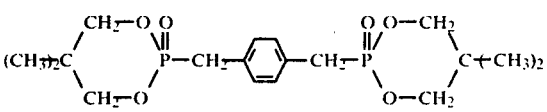

5. The compound of claim 1 having the formula:

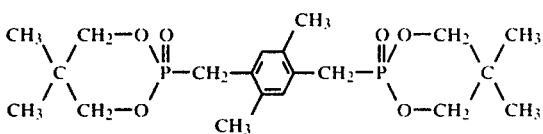

6. The compound of claim 1 having the formula:

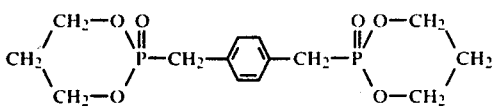

7. The compound of claim 1 having the formula:

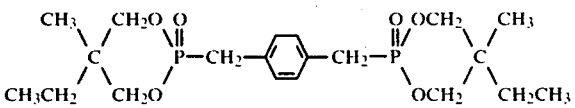

* * * * *